United States Patent [19]

Wilson et al.

[11] Patent Number: 4,861,457

[45] Date of Patent: Aug. 29, 1989

[54] CRYSTALLINE GALLOPHOSPHATE COMPOSITIONS

[75] Inventors: Stephen T. Wilson, Shrub Oak; Naomi A. Woodard, Peekskill; Edith M. Flanigen, White Plains, all of N.Y.

[73] Assignee: UOP, Des Plaines, Ill.

[21] Appl. No.: 256,753

[22] Filed: Oct. 12, 1988

Related U.S. Application Data

[62] Division of Ser. No. 53,735, May 26, 1987, Pat. No. 4,799,942, which is a division of Ser. No. 811,282, Dec. 20, 1985, Pat. No. 4,690,808.

[51] Int. Cl.[4] ............... C10G 11/04; C10G 47/04; C07C 2/10; C07C 2/18
[52] U.S. Cl. ..................... 208/46; 208/111; 208/114; 208/120; 208/143; 208/135; 208/216 R; 208/217; 208/251 H; 208/254 H; 585/466; 585/467; 585/480; 585/527
[58] Field of Search ............... 208/46, 114, 112, 143, 208/135, 122, 217, 251 H, 254 H, 111, 120, 216 R; 585/527, 480, 466, 467

[56] References Cited

U.S. PATENT DOCUMENTS

| | | | |
|---|---|---|---|
| 4,310,440 | 1/1982 | Wilson et al. | 208/112 |
| 4,440,871 | 4/1984 | Lok et al. | 208/114 |
| 4,690,808 | 9/1987 | Wilson et al. | 502/208 |
| 4,735,806 | 4/1988 | Flanigen et al. | 502/214 |
| 4,799,942 | 1/1989 | Wilson et al. | 55/35 |

*Primary Examiner*—Anthony McFarlane
*Attorney, Agent, or Firm*—Thomas K. McBride; Eugene I. Snyder; Frank S. Molinaro

[57] ABSTRACT

A novel family of crystalline, microporous gallophosphate compositions is synthesized by hydrothermal crystallization at elevated temperatures from gallophosphate gels containing a molecular structure-forming template. The family comprises distinct species, each with a unique crystal structure. Calcination removed volatile extraneous matter from the intracrystalline void space and yields microporous crystalline adsorbents with pores, the dimensions of which vary, among the individual species, from about 3A to 10A in diameter. The compositions represent a new class of adsorbents of the molecular sieve type, and also exhibit properties somewhat analogous to zeolitic molecular sieves which render them useful as catalysts or catalyst based in chemical reactions such as hydrocarbon conversion.

11 Claims, No Drawings

CRYSTALLINE GALLOPHOSPHATE COMPOSITIONS

This application is a division of prior U.S. application Ser. No. 053,735, filed May 26, 1987, now U.S. Pat. No. 4,799,942, and which is a division of application Ser. No. 811,282, filed Dec. 20, 1985, now U.S. Pat. No. 4,690,808.

The present invention relates in general to a novel family of crystalline gallophosphate compositions of the general formula $GaPO_4$ and to the method for their synthesis. More particularly it relates to crystalline microporous gallophosphate compositions and to hydrothermal processes for preparing same.

Molecular sieves of the crystalline zeolite type are well known in the art and now comprise over 150 species of both naturally occurring and synthetic compositions. In general the crystalline zeolites are aluminosilicates whose frameworks are formed from $AlO_4$- and $SiO_4$ tetrahedra joined by the sharing of oxygen atoms and characterized by having pore openings of uniform dimensions, having a significant ion-exchange capacity and being capable of reversibly desorbing an adsorbed phase which is dispersed through the internal voids of the crystal without displacing any atoms which make up the permanent crystal structure.

Other crystalline microporous phases which are not zeolitic, i.e. do not contain $AlO_4$- tetrahedra as essential framework constituents, but which exhibit the ion exchange and/or adsorption characteristics of the zeolitic phases are also known. Metallorganosilicates which are said to possess ion-exchange properties, have uniform pores and are capable of reversibly adsorbing molecules having molecular diameters of about 6A or less are reported in U.S. Pat. No. 3,941,871 issued Mar. 2, 1976 to Dwyer et al. Also a pure silica polymorph having molecular sieving properties and a neutral framework containing no cations or cation sites is defined in U.S. Pat. No. 4,061,724 issued Dec. 6, 1977 to R. W. Grose et al.

The chemistry of aluminum phosphates has been reviewed by J. H. Morris et al. (Chem. Soc. Rev., 6, 173 (1977)). The phosphates with an $Al_2O_3:P_2O_5$ molar ratio of 1:1 are the most common, and have been the most widely studied. Anhydrous $AlPO_4$ is isoelectronic and isostructural with silica and exists in quartz (as berlinite), tridymite, and cristobalite forms possessing frameworks of alternating $AlO_4$ and $PO_4$ tetrahedra. In addition to these, F. D.'Yvoire [Bull. Soc. Chim. France, 1762 (1961)] has described five anhydrous crystalline $AlPO_4$ forms which have no silica analogs.

Two hydrates of $AlPO_4$ with the stoichiometry $AlPO_4.2H_2O$, metavariscite and variscite, occur in natural and synthetic forms. Their structures were determined by Kniep and coworkers (Acta Crysta., B29, 2292 (1973); ibid., B33 263 (1977), and both can be described as frameworks of alternating octahedral $AlO_4(H_2O)_2$ and tetrahedral $PO_4$ units. In both the metavariscite and variscite structures the $H_2O$ is chemically bound to the Al and, although small amounts of this water can be removed reversibly, complete dehydration is irreversible and leads to significant structural changes and the formation of anhydrous $AlPO_4$ phases.

In addition to these, six crystallographically unique, metastable hydrates have been synthesized by F. D'Yvoire (ibid.). Of these, four are reported to be reversibly dehydrated under mild conditions to yield anhydrous phases, but in each case significant changes in framework topology occurred. These changes were reported to be reversible by rehydration. It is possible therefore that the interaction between water and these aluminophosphate phases results in chemical bonding, such as the formation of $AlO_4(H_2O_2)_2$ octahedra, rather than physisorption.

The hydrothermal synthesis of aluminophosphates in the presence of various alkali metal, alkaline earth, and $NH_4$ cations has been reported by Haseman and coworkers (Soil Sci. Soc. Proceed., 76 (1950); Soil Sci., 70, 257-271 (1950)), by Cole and Jackson (J. Phys. Chem.), 54, 128-142 (1950)), and by Golub and Boldog (Russ. Jour, Inorg, Chem., 21, 45 (1976)). A variety of known minerals (e.g., palmierite, taranakite, wavellite, variscite) and many novel crystalline materials were obtained. Virtually all of these materials had Al/P ratios different from 1.0. Although most of the products had appreciable $H_2O$ content only one product was examined by X-ray powder diffraction after dehydration. This product, taranakite, became amorphous at 125° C. The stability of the other phases is unknown.

R. M. Barrer and D. J. Marshall (J. Chem. Soc., 616 (1965)) attempted to substitute P for Si during hydrothermal crystallization of mixed frameworks analogous to aluminosilicates. The crystalline products obtained from synthesis mixtures containing sources of Al, Si, and P were predominately aluminosilicates (e.g., montmorillonite, analcite, and cancrinite) and phosphates (e.g., hydroxyapatite). Several unidentified crystalline solids were observed, characterized solely by their X-ray powder diffraction patterns. Evidence for phosphorus incorporation in the aluminosilicate structures or silicon incorporation in the hydroxyapatites was not obtained, however.

G. Kuehl has used phosphate as a complexing ion for aluminum in the hydrothermal synthesis of certain zeolites (Proceedings of the London Conf. on Molecular Sieves, April 1967, p. 85; Inorg. Chem., 10, 2488 (1971)). Presumably the phosphate complexes some of the aluminum, lowering the effective concentration of the more reactive hydroxoaluminate species in the reaction mixture and, thereby, increases the ratio of silicate to hydroxoaluminate. The zeolite products had a higher Si/Al ratio than normal and presumably no incorporation of P into the zeolite frameworks was observed. In one case, a high-silica form of zeolite A contained phosphate intercalated in the sofalite cages.

In an attempt to isolate the aluminophosphate species formed when phosphate is added to a zeolite synthesis mixture, G. Kuehl prepared the crystalline compounds $[(CH_3)_4N]_3[Al(PO_4)_2]$ $XH_2O$ where X=10, 4, and 1.5. They were characterized by X-ray powder diffraction, thermal, and elemental analysis, and were described as salts containing isolated $Al(PO_4)_2(OH_2)_x{}^{3-}$ units. Removal of all the $H_2O$ caused the decomposition of these compounds (U.S. Pat. No. 3,386,801 (1968); J. Inorg. Nucl. Chem., 31, 1943 (1969)).

U.S. Pat. No. 4,310,440 discloses a novel class of aluminophosphates having an essential crystalline framework structure whose chemical composition expressed in terms of molar ratios of oxides, (anhydrous basis) is $$Al_2O_3:1.0\pm0.2P_2O_5$$

said framework structure being microporous in which the pores are uniform and in each species have nominal diameters within the range of from 3 to 10 Angstroms; an intracrystalline adsorption capacity for water at 4.6 torr and 24° C. of at least 3.5 weight percent, the adsorption of water being completely reversible while retaining the same essential framework topology in both the hydrated and dehydrated state.

U.S. Pat. No. 4,440,871 discloses a novel class of crystalline microporous silicoaluminophosphates the pores of which are uniform and have nominal diameters of greater than about 3 Angstroms and whose essential empirical chemical composition in the as-synthesized and anhydrous form is $$mR: (Si_xAl_yP_z)_2$$

wherein "R" represents at least one organic templating agent present in the intracrystalline pore system; "m" has a value of from 0.02 to 0.3; "m" represents the moles of "R" present per mole of $(Si_xAl_yP_2)_2$; and "x", "y" and "z" represent the mole fractions of silicon, aluminum and phosphorus respectively, present as tetrahedral oxides.

Several reports of gallim substitutoion have been made. In Barrer, R. M., Baynham, J. W., Bultitude, F. W., and Meier, W. M., J. Chem. Soc., (1959), 195–208, it is reported that Al was replacedwith Ga in Na gels of the zeolite types. It was reported that a Na gallosilicate of the thompsonite-type zeolite was made and that Na gallogermanate analogs of thompsonite, faujasite, sodalite, zeolites were made. In Tananaev, I. V. and N. N. Chudinova, Russian J. Inor. Chem. (9), (1964), 135–138, it was reported that stoichiometric, precipitated, amorphous GaPO4 (+3H2O) was made from GaCl3 and H3PO4 or NaH2PO4. The products of a dehydration at 80°–140° C. were amorphous and heating to 540° C. converted it to a low cristobalite structure. Heating above 940° C. gave a high-cristobalite intermediate, but 1000° C. heating and slow cooling to ambient gave a berlinite (quartz). In Selbin, J., and Mason, R. B., J. Inorg. Nucl. Chem., (1961), (20), 222–228, Ga,Si zeolites were prepared in a Na system including 13X, sodalite, and an unidentified phase. The 13X analog had molecular sieve properties, as measured by uptake of n-heptane, while others did not. Also, a Ga,Al,Si (Na) analog of 13X zeolite was reported and adsorption was confirmed by uptake of n-heptane. In Mooney-Slater, R. C. L., (1966), Acta Cryst., (20), 526–534, crystals were prepared of a hydrated gallium phosphate of formula GaPO4-2H2O which lost water between 100° and 370° C. after which the product was found to be amorphous. The author reported an X-ray single crystal structure of GaPO4-2H2O and concluded it to be a hydrated basic salt in which the gallium is part of an infinite hydrated hydroxy chain complex rather than functioning as a single ion. In Pluth, J. J., Smith, J. V., Bennett, J. M., and Cohen, J. P., Acta Cryst., (1984), (C40), 2008–2011, The crystal structure of NH4Al2(OH)(H2O)(PO4)2-H2O was reported and found it to be structurally related to the GaPO4-2H2O of Mooney-Slater which appeared to have H3O and Ga in place of the NH4 and Al in the above formula. Structural relation to the K,Fe,PO4 species, leucophosphate, was also shown. This hydrated NH3,Al,PO4 species, also referred to as AlPO4-15, first becomes amorphous then converts to a form of cristobalite upon heating to remove the NH3 and water. In Eshchenko, L. S., Pechkovskii, V. V., and Stanovaya, L. S., Inor. Materials (Russian), (14), (1978), 723–726, investigations were reported of an orthorhombic form of GaPO4-2H2O which found it structurally like the aluminophosphate hydrate denoted variscite. Thermal analysis showed dehydration of the GaPO4-2H2O to be complete by 190° C. They also found that heating to 190° C. or above resulted in conversion to the anhydrous quartz-like crystalline phase of GaPO4.

A recent report of gallium phosphate compositions may be found in "Some Gallium Phosphate Frameworks Related to the Aluminum Phosphate Molecular Sieves: X-Ray Structural Characterization of {Pr—I—NH3} [Ga4(PO4)4·OH}·H2O", by John B. Parise, J. Chem. Soc., CHEM. COMMUN., pages 606–607 May 1, 1985. This report describes members of the generic class of gallophosphates of the instant invention.

DETAILED DESCRIPTION OF THE INVENTION

The novel class of gallophosphate compositions are characterized as having a crystalline framework structure whose chemical composition expressed in terms of molar ratios of oxides, is $$mR:Ga_2O_3:1.0\pm0.2P_2O_5$$

wherein "R" represents at least one organic templating agent present in the intracrystalline pore system; "m" has a value of from 0.02 to 0.3; "m" represents the moles of "R"; and said framework structure being microporous in which the pores in each species have nominal diameters within the range of from 3 to 10 Angstroms. In one embodiment the GaPO4 compositions are calcined to remove at least some template "R" and the intracrystalline adsorption capacity for oxygen at 100 torr and −183° C. is at least 3 weight percent. The instant compositions may also be characterized by their retaining at least 50 percent of their crystallinity after calcination. The instant compositions retain at least 50 percent of their original crystallinity, preferably at least 70 percent and most preferably at least 80 percent of the crystallinity of the original starting method when calcined at temperatures above about 300° C. for at least one hour.

The individual gallophosphate species of the instant invention may be characterized by their x-ray diffraction patterns. The following x-ray diffraction patterns are representative of x-ray diffraction patterns which may be characteristic of particular gallophosphate species:

TABLE A

| $2\theta$ | d(A) | Relative Intensity |
|---|---|---|
| 8.1–8.3 | 10.9–10.6 | VS |
| 9.6–9.9 | 9.2–9.0 | VW–W |
| 10.4–10.6 | 8.52–8.38 | VW–M |
| 15.1–15.4 | 5.88–5.77 | VW–W |
| 21.8–22.0 | 4.08–4.03 | VW–W |
| 22.4–22.7 | 3.97–3.92 | VW–W |

TABLE B

| $2\theta$ | d(A) | Relative Intensity |
|---|---|---|
| 7.4 | 12.0 | VS |
| 18.2 | 4.85 | W |
| 21.5 | 4.13 | W |
| 22.3 | 3.99 | W |
| 23.8 | 3.73 | W |

TABLE B-continued

| $2\theta$ | d(A) | Relative Intensity |
|---|---|---|
| 29.2 | 3.06 | W |

The present gallophosphates are prepared by hydrothermal crystallization of a reaction mixture prepared by combining a reactive source of phosphate, a gallium compound and water and at least one structure-directing or templating agent which can include an organic amine and a quaternary ammonium salt. In the as-synthesized form the structure-directing agent is contained within the framework structure of the gallophosphate in amounts which vary from species to species but usually does not exceed one mole per mole of $Ga_2O_3$ thereof. This structure-directing agent is readily removed by water washing or calcination and does not appear to be an essential constituent of the product gallophosphate.

Broadly, the preparative process comprises forming a reactive mixture which in terms of molar ratios of oxides is $$Ga_2O_3:1\pm0.5P_2O_5:7\text{-}100H_2O$$

and containing an effective amount ot template preferably from about 0.2 to 10.0 moles of templating agent per mole of $Ga_2O_3$. It has been observed that the amount of template is related, at least in part, to the gallium source. For example, the use of an acid salt of gallium may enable the use of a higher effective amount of template to form the instant gallophosphate compositions. The reaction mixture is placed in a reaction vessel inert toward the reactin system and heated at a temperature of at least about 100° C., preferably between 100° C. and 300° C., until crystallized, usually a period from 2 hours to 2 weeks. The solid crystalline reaction product is then recovered by any convenient method, such as filtration or centrifugation, washed with water and dried at a temperature between ambient and 110° C. in air.

In a preferred crystallization method the source of phosphate is phosphoric acid, and source of gallium is gallium (III) hydroxide, gallium (III) sulfate, or other soluble gallium (III) salts, the temperature is 125° C. to 200° C., and the crystallization time is from one to seven days. The preferred ratio of oxides in the reaction mixture is $$Ga_2O_3:0.8\text{-}1.2P_2O_5:25\text{-}75H_2O$$

in general the most preferred reaction mixture contains per mole of $Ga_2O_3$ from about 0.5–8.0 moles of templating agent, from 40–75 moles of water and about 1.0 mole of $P_2O_5$.

Not all templating agents suitably employed in the preparation of certain species of gallophosphates of this invention are suitable for the preparation of all members of the generic class. The relationship of specific templating agents to the individual product species is apparent from the illustrative Examples set forth hereinafter. The template may be selected from the group consisting of tetrapropylammonium hydroxide; tetraethylammonium hydroxide; tripropylamine; triethylamine; triethanolamine; piperidine; cyclohexylamine; 2-methyl pyridine; N,N-dimethylbenzylamine; ethylenediamine; pyrolidine; N,N-diethylethanolamine; dicyclohexylamine; N,N-dimethylethanolamine; choline; N,N dimethylpiperazine; 1,4-diazabicyclo(2,2,2)octane; N-methyldiethanolamine; N-methylethanolamine; N-methylpiperidine; 3-methylpiperidine; N-methylcyclohexylamine; 3-methylpyridine; 4-methylpyridine; quinuclidine; and N,N'-dimethyl-1,4-diazabicyclo(2,2,2)octane dihydroxide.

The most suitable phosphorus source is phosphoric acid, although organic phosphates and conventional phosphorus salts may be employed.

The gallium source may be a gallium (III) hydroxide, gallium alkoxides, gallium carboxylates (e.g., gallium oxalate and gallium acetate), gallium trioxide ($Ga_2O_3$), gallium (III) sulfate or other suitable gallium sources, including organogallium compounds.

The method of preparation and the physical and chemical properties of certain members of the present class of novel gallophosphates are illustrated and characterized, respectively, in the following examples. The species compounds are denominated as $GaPO_4$-n wherein "n" is a small letter specific to each individual member as prepared herein.

EXAMPLE 1

(a) $GaPO_4$-a was prepared by the following procedure: 6.5 grams of gallium (III) sulfate hydrate ($Ga_2(SO_4)_3.12H_2O$) was dissolved in 6.5 grams $H_2O$ and added to a solution containing 2.2 grams of quinuclidine ($C_7H_{13}N$) which was previously dissolved in 2.0 grams of $H_2O$. Orthophosphoric acid (2.3 grams of 85% orthophosphoric acid ($H_3PO_4$)) was mixed into the initial mixture, followed by the addition of another 4.4 grams of quinuclidine. The resulting mixture was blended to form a final reaction mixture with a composition in terms of molar oxide ratios of:

$$6.0C_7H_{13}N:1.0Ga_2O_3:1.0P_2O_5:3.0H_2SO_4:64H_2O$$

A portion of the reaction mixture was placed in a sealed stainless steel pressure vessel lined with polytetrafluoroethylene and heated in an oven at 200° C. for 24 hours. The solid product was recovered by filtration, water washed, and dried in air at room temperature. A small amount of an impurity was present in the solid product but the major component, $GaPO_4$-a, had an x-ray powder diffraction pattern characterized by the following data (Table I):

TABLE I

| $2\theta$ | d(A) | $(I/I_o) \times 100$ |
|---|---|---|
| 8.2 | 10.74 | 100 |
| 9.8 | 9.07 | 2 |
| 10.5 | 8.41 | 1 |
| 13.4 | 6.62 | 1 |
| 14.3 | 6.20 | 3 |
| 15.2 | 5.83 | 1 |
| 16.5 | 5.37 | 5 |
| 17.3 | 5.12 | 3 |
| 17.8 | 4.99 | 1 |
| 19.6 | 4.53 | 2 |
| 21.9 | 4.06 | 9 |
| 22.5 | 3.95 | 5 |
| 24.3 | 3.66 | 1 |
| 24.8 | 3.58 | 4 |
| 27.1 | 3.29 | 1 |
| 28.8 | 3.10 | 5 |
| 29.2 | 3.05 | 1 |
| 30.0 | 2.98 | 2 |
| 30.6 | 2.92 | 1 |
| 31.8 | 2.81 | 2 |
| 33.3 | 2.69 | 1 |
| 33.8 | 2.66 | 4 |
| 35.0 | 2.56 | 1 |
| 36.4 | 2.468 | 1 |

TABLE I-continued

| 2θ | d(A) | (I/Io) × 100 |
|---|---|---|
| 36.8 | 2.442 | 1 |
| 37.1 | 2.426 | 1 |
| 38.4 | 2.346 | 1 |
| 39.9 | 2.262 | 1 |
| 47.7 | 1.919 | 1 |
| 48.3 | 1.883 | 1 |
| 50.0 | 1.825 | 1 |
| 51.2 | 1.784 | 1 |
| 51.7 | 1.768 | 1 |
| 53.2 | 1.722 | 1 |
| 54.4 | 1.688 | 1 |

(b) Another portion of the reaction mixture from part (a) above was heated at 150° C. for 24 hours and the solid product isolated in a similar manner. Again the solid was predominanately GaPO$_4$-a with an x-ray powder diffraction pattern essentially as set forth above in Table I. By chemical analysis the product composition was 37.4 wt.% P$_2$O$_5$, 47 wt.% Ga$_2$O$_3$, 9.5 wt.% Carbon, 1.4 wt.% Nitrogen, and 15.7 wt.% LOI (Loss On Ignition), corresponding to a molar oxide ratio product composition of:

$$0.43C_7H_{13}N{:}0.95Ga_2O_3{:}1.00P_2O_5{:}0.66H_2O$$

which corresponds to the formula (anhydrous basis):

$$0.11(C_7H_{13}N)(Ga_{0.49}P_{0.51})O_2$$

(c) A portion of the solid product from part (b) above was activated under vacuum at 425° C. for 2 hours in a standard McBain-Bakr gravimetric adsorption apparatus and the following adsorption data were obtained (an additional 350° C. activation of the sample followed each adsorbate):

| Adsorbate | Kinetic Diameter, (A) | Pressure, (Torr) | Temp., (°C.) | Wt. % Adsorbed |
|---|---|---|---|---|
| O$_2$ | 3.46 | 102 | −183 | 11.7 |
| O$_2$ | 3.46 | 698 | −183 | 12.3 |
| n-hexane | 4.3 | 44 | 23 | 4.2 |
| isobutane | 5.0 | 501 | 22 | 0.2 |
| H$_2$O | 2.65 | 4.6 | 23 | 13.7 |
| H$_2$O | 2.65 | 19.6 | 23 | 17.0 |

The adsorption of n-hexane and the essentially nil adsorption of isobutane show the pore size of the product to be at least 4.3 Å and less than 5.0 Å.

EXAMPLE 2

(a) In another preparation of GaPO$_4$-a, gallium (III) hydroxide was added to a solution consisting of tetramethylammonium hydroxide pentahydrate (TMAOH.5H$_2$O) dissolved in H$_2$O. Orthophosphoric acid (85% H$_3$PO$_4$)was then added to form a final reaction mixture having a composition expressed in molar oxide ratios of:

$$1.0TMAOH{:}1.0Ga_2O_3{:}1.0P_2O_5{:}40H_2O$$

The reaction mixture was divided into several portions. Each portion was sealed in stainless steel pressure vessels lined with polytetrafluoroethylene and each portion heated in an oven at one of the following: (a) 150° C. for 24 hours; (b) 150° C. for 96 hours; (c) 200° C. for 24 hours; and (d) 200° C. for 96 hours. The solid products from (a), (b), (c) and (d) were recovered by centrifugation, washed with water, and dried in air at room temperature (18° C.–22° C.). The resulting x-ray powder diffraction pattern of the product of each preparation corresponded to a product mixture, the major portion of each being characterized by an x-ray powder diffraction pattern essentially the same as Table I, above, corresponding to GaPO$_4$-a. The product mixture also contained gallium(III) hydroxide.

(b) SEM analysis of the solid product from preparation (d) of part (a), above, showed a large fraction of the sample to be crystals with a hexagonal prism morphology with lengths ranging up to 100 microns. EDAX spot probe analyses of these crystals are consistent with the presence of both elements, Ga and P, in roughly equal amounts in the crystals.

(c) A portion of the solid from preparation (a) of part (a), above, was subjected to DTA/TGA thermal analysis. Slow heatup (5° C./min.) in flowing air resulted in a strong, sharp exotherm accompanied to breakdown, release, and combustion of the tetramethylammonium species (template) entrapped within the GaPO$_4$-a gallophosphate molecular sieve framework structure as a result of its preparation.

EXAMPLE 3

(a) Using a procedure and reagents similar to that of Example 2, above, but with the use of an aqueous solution of 40 wt.% tetraethylammonium hydroxide (TEAOH) instead of the tetramethylammonium hydroxide (TMAOH.5H$_2$O), a reaction mixture was prepared having a chemical composition in molar oxide ratios of:

$$1.0TEAOH{:}1.0Ga_2O_3{:}1.0P_2O_5{:}40H_2O$$

A portion of this mixture was heated at 150° C. for 97 hours. This heating and subsequent solids recovery were by the methods described in Example 2. The major component of the product was GaPO$_4$-a and was characterized by the x-ray powder diffraction pattern of Table I, above. As observed in Example 2, some of the gallium(III) hydroxide starting material was present in the solid product. Chemical analysis of the product gave 54.6 wt.% Ga$_2$O$_3$, 29.4 wt.% P$_2$O$_5$, 8.2 wt.% Carbon, 1.2 wt.% Nitrogen and 16.6 wt.% LOI. In terms of the components identified by the x-ray powder diffraction pattern, the analysis corresponds to a mixture of 15.8 wt.% starting gallium(III) hydroxide expressed as Ga$_2$O$_3$ with the remaining 84.2 wt.% of the solid product being GaPO$_4$-a having a molar oxide ratio composition of:

$$0.41TEAOH{:}1.0Ga_2O_3{:}1.0P_2O_5{:}0.72H_2O$$

which corresponds to the formula (anhydrous basis):

$$0.10TEAOH{:}(Ga_{0.50}P_{0.50})O_2$$

(b) Another portion of the reaction mixture of part (a) above was similarly heated at 150° C. for 24 hours. The x-ray pattern of the resulting solid also indicated it to be predominantely GaPO$_4$-a in the presence of some remaining gallium (III) hydroxide. A portion of the sample was placed under vacuum and heated from 25° to 300° C. at a 20 degrees/min. and from 300° to 400° C. at 10 degrees/min. and held one hour at 400° C. before returning to room temperature. An x-ray pattern was then obtained of this vacuum calcined product which indicated that the GaPO₄-a component of the sample remained essentially fully crystalline, although some shifts of individual peak intensities and positions resulted from the removal of entrapped species.

(c) The species GaPO₄-a is a crystalline gallophosphate whose essential framework structure has a chemical composition, expressed in terms of molar oxide ratios, of:

$$Ga_2O_3:1\pm0.2P_2O_5$$

All of the GaPO₄-a compositions for which the x-ray powder diffraction patterns have been obtained have a generalized x-ray diffraction as set forth in pattern Table II below:

TABLE II

| 2θ | d(A) | 100 × (I/Io) |
|---|---|---|
| 8.1–8.3 | 10.9–10.6 | 100 |
| 9.6–9.9 | 9.2–910 | 2–18 |
| 10.4–10.6 | 8.52–8.38 | 1–38 |
| 13.2–13.5 | 6.70–6.57 | 1–4 |
| 14.1–14.4 | 6.28–6.17 | 1–9 |
| 15.1–15.4 | 5.88–5.77 | 1–14 |
| 16.3–16.6 | 5.42–5.33 | 2–6 |
| 17.2–17.5 | 5.15–5.08 | 1–6 |
| 17.6–18.0 | 5.03–4.94 | 1–13 |
| 19.4–19.8 | 4.56–4.49 | 1–13 |
| 21.8–22.0 | 4.08–4.03 | 7–15 |
| 22.4–22.7 | 3.97–3.92 | 4–13 |
| 24.2–24.5 | 3.68–3.63 | 1–3 |
| 24.7–25.0 | 3.60–3.56 | 2–5 |
| 27.1–27.2 | 3.29–3.28 | 1–6 |
| 28.6–29.0 | 3.12–3.08 | 3–6 |
| 29.2–29.5 | 3.05–3.03 | 1–3 |
| 29.9–30.2 | 2.99–2.96 | 2–5 |
| 30.4–30.8 | 2.94–2.90 | 1–7 |
| 31.5–32.1 | 2.84–2.79 | 1–9 |
| 33.2–33.4 | 2.70–2.69 | 1–3 |
| 33.8 | 2.655–2.654 | 3–4 |
| 35.0–35.1 | 2.564–2.557 | 0–1 |
| 36.4 | 2.468–2.467 | 0–1 |
| 36.8 | 2.442–2.440 | 0–1 |
| 37.1 | 2.426–2.425 | 0–1 |
| 38.4–38.6 | 2.346–2.334 | 0–2 |
| 39.9–40.1 | 2.262–2.250 | 0–1 |
| 42.0 | 2.151–2.150 | 0–1 |
| 43.1–43.3 | 2.100–2.088 | 0–2 |
| 44.0–44.3 | 2.059–2.046 | 0–1 |
| 44.9–45.3 | 2.020–2.002 | 0–1 |
| 45.6 | 1.991–1.990 | 0–1 |
| 47.3–47.7 | 1.920–1.907 | 0–2 |
| 48.0–48.3 | 1.897–1.883 | 0–2 |
| 49.9–50.0 | 1.827–1.825 | 0–1 |
| 51.2 | 1.785–1.782 | 0–1 |
| 51.6–51.7 | 1.771–1.767 | 0–2 |
| 53.2–53.5 | 1.723–1.713 | 0–1 |
| 54.4 | 1.688–1.687 | 0–1 |

A characteristic x-ray pattern for GaPO₄-a contains at least the d-spacings set forth in Table A below:

TABLE A

| 2θ | d(A) | Relative Intensity |
|---|---|---|
| 8.1–8.3 | 10.9–10.6 | VS |
| 9.6–9.9 | 9.2–9.0 | VW–W |
| 10.4–10.6 | 8.52–8.38 | VW–M |
| 15.1–15.4 | 5.88–5.77 | VW–W |
| 21.8–22.0 | 4.08–4.03 | VW–W |
| 22.4–22.7 | 3.97–3.92 | VW–W |

EXAMPLE 4

(a) GaPO₄-b was prepared by the following procedure: 7.2 grams of gallium (III) sulfate hydrate (Ga₂(SO₄)₃.12H₂O) was dissolved in 8.7 grams of H₂O to which was added 2.6 grams of 85% orthophosphoric acid (H₃PO₄). 11.1 grams of tri-n-propylamine (C₉H₂₁N) was added to this mixture to form a final reaction mixture having a composition in terms of molar oxide ratios of:

$$7.0C_9H_{21}N:1.0Ga_2O_3:1.0P_2O_5:3.0H_2SO_4:60H_2O$$

A portion of the reaction mixture was placed in a sealed stainless steel pressure vessel lined with polytetrafluoroethylene and heated in an oven at 150° C. for 24 hours. The solid product was recovered by centrifugation and filtration. The solid product was water washed, and dried in air at room temperature. The product was well crystallized as shown by the x-ray powder diffraction pattern characterized by the following data (Table III):

TABLE III

| 2θ | d(A) | (I/Io) × 100 |
|---|---|---|
| 7.4 | 11.96 | 100 |
| 10.7 | 8.25 | 5 |
| 13.1 | 6.79 | 2 |
| 18.3 | 4.85 | 5 |
| 21.5 | 4.13 | 8 |
| 22.3 | 3.99 | 7 |
| 22.7 | 3.92 | 1 |
| 23.8 | 3.73 | 7 |
| 24.8 | 3.60 | 4 |
| 26.2 | 3.40 | 3 |
| 29.2 | 3.06 | 10 |
| 30.7 | 2.91 | 3 |
| 31.1 | 2.88 | 1 |
| 32.3 | 2.78 | 1 |
| 32.6 | 2.75 | 1 |
| 34.3 | 2.62 | 1 |
| 36.5 | 2.461 | 1 |
| 37.1 | 2.424 | 2 |
| 37.7 | 2.386 | 1 |
| 50.5 | 1.808 | 2 |

A characteristic GaPO₄-b x-ray pattern contains at least the d-spacings set forth in Table B below:

TABLE B

| 2θ | d(A) | Relative Intensity |
|---|---|---|
| 7.4 | 12.0 | VS |
| 18.2 | 4.85 | W |
| 21.5 | 4.13 | W |
| 22.3 | 3.99 | W |
| 23.8 | 3.73 | W |
| 29.2 | 3.06 | W |

(b) A portion of the solid product described above was subjected to DTA/TGA thermal analysis. Slow heatup (10 deg. °C./min.) in flowing air resulted in a total weight loss by 650° C. of 14.3 wt.%. The first 6.5 wt.% loss occurred in gradual dstages up to 390° C., apparently representing loss of water and perhaps some tri-n-propylamine. Most of the remaining 7.8 wt.% loss occurred in a rapid step from 390° to 450° C. accompanied by a sharp, strong exotherm characteristic of breakdown, release, and combustion of the organic species (tri-n-propylamine) entrapped within the crystalline gallophosphate molecular sieve framework structure.

Chemical analysis of another portion of the same solid product found: 49.4 wt.% Ga₂O₃, 32.2 wt.% P₂O₅, 0.89 wt.% Nitrogen, and 7.6 wt.% Carbon. This together with the 650° C. total loss of 14.3 wt.% from the above thermal analysis, corresponds to a molar oxide ratio composition of:

0.07C$_9$H$_{21}$N:1.0Ga$_2$O$_3$:0.86P$_2$O$_5$:0.88H$_2$O which is represented by the formula (anhydrous basis):

0.07C$_9$H$_{21}$N:(Ga$_{0.54}$P$_{0.46}$)O$_2$ (c) Another portion of the reaction mixture described in part (a), above, was heated in an oven at 200° C. for 24 hours. The solid product was isolated as described in Part (a), above. The x-ray powder diffraction pattern indicated the product to consist principally of the quartz-like analog of gallium phosphate.

PROCESSES EMPLOYING GaPO$_4$ COMPOSITIONS

Among the hydrocarbon conversion reactions which may be catalyzed by the instant gallophosphate compositions are cracking, hydrocracking, alkylation of both the aromatic and isoparaffin types, isomerization including xylene isomerization, polymerization, reforming, hydrogenation, dehydrogenation, transalkylation, dealkylation and hydration.

Using gallophosphate catalyst compositions which contain a hydrogenation promoter such as platinum or palladium, heavy petroleum residual stocks, cyclic stocks and other hydrocrackable charge stocks can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The gallophosphate catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e., those containing hydrogenation promoters, are also useful in hydroisomerization processes in which feedstocks such as normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (H/Hc) of between 1 and 5.

At somewhat higher temperatures, i.e., from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of C$_7$–C$_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0 are suitable.

The present gallophosphate catalysts may be employed in the conversion of alkylaromatic compounds, particularly the catalytic disproportionation of toluene, ethylene, trimethyl benzenes, tetramethyl benzenes and the like. In the disproportionation process isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not be present in the process. The process temperature is generally from about 400° to 750°0 F. with pressures in the range of 100 to 2000 p.s.i.g. and LHSV values in the range of 0.1 to 15.

Catalytic cracking processes may be carried out with gallophosphate compositions using feedstocks such as gas oils, heavy naphthas, deasphalted crude oil residua, etc. with gasoline being the principal desired product. The process conditions employed for catalytic cracking processes are well known in the art. Temperature conditions of 850° to 1100° F., LHSV values of 0.5 to 10 and pressure conditions of from about 0 to 50 p.s.i.g. are typically employed.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the gallophosphate catalyst compositions in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°–1000° F. are employed at moderate hydrogen pressures of about 300–1000 p.s.i.g., other conditions being similar to those described above for catalytic hydrocracking. Preferred catalysts are of the same type described above in connection with catalytic dehydrocyclization. Particularly desirable dealkylation reactions include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of catalysts for hydrocracking. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock.

The present gallophosphate compositions can be used in the same conventional molecular sieving processes as heretofore have been carried out using aluminosilicate or aluminophosphate molecular sieves. For use in these processes the gallophosphate compositions are preferably activated to remove any molecular species which may be present in the intracrystalline pore system as a result of synthesis or otherwise. It is sometimes necessary to thermally destroy organic species present in as-synthesized gallophosphate compositions since some are too large to be desorbed by conventional means.

The gallophosphate compositions are useful as adsorbents and are capable of separating mixtures of molecular species both on the basis of molecular size (kinetic diameters) and degree of polarity of the involved molecules. In the case of selective adsorption based on molecular size, the gallophosphate adsorbent is chosen in view of the dimensions of its pores such that at least the smallest molecular species of the mixture can enter the intracrystalline void space while at least the largest specie is excluded. In separations based on degree of polarity, the more hydrophilic gallophosphate species will preferentially adsorb the more polar molecular species of a mixture having different degrees of polarity even though both molecular species can enter the gallophosphate pore system.

What is claimed is:

1. A process for converting a hydrocarbon comprising contacting the hydrocarbon under hydrocarbon converting conditions with a crystalline gallophosphate composition having a framework structure whose chemical composition expressed in terms of mole ratios of oxides is $mR:Ga_2O_3:1.0\pm0.2P_2O_5;$ wherein "R" represents at least one organic templating agent present in the intracrystalline pore system, "m" has a value of from 0.02 to 0.3 and represents the moles of "R"; said framework structure being microporous in which the pores have nominal diameters within the range of about 3 to about 10 Angstroms to give a hydroconverted product.

2. A process for convertoing a hydrocarbon comprising contacting the hydrocarbon under hydrocarbon converting conditions with a crystalline gallophosphate compositin having a framework structure whose chemical composition expressed in terms of mole ratios of oxide is $Ga_2O_3:1.0\pm0.2P_2O_5;$ characterized in that the framework structure is microporous, the pores having a nominal diameter within the range of about 3 to about 10 Angstroms, and the framework structure retains at least 50 percent of its crystallinity upon calcination at a temperature of at least 300° C. for at least one hour to give a hydroconverted product.

3. Process according to claim 1 or 2 wherein the hydrocarbon conversion process is cracking.

4. Process according to claim 1 or 2 wherein the hydrocarbon conversion process is hydrocracking.

5. Process according to claim 1 or 2 wherein the hydrocarbon conversion process is hydrogenation.

6. Process according to claim 1 or 2 wherein the hydrocarbon conversion process is polymerization.

7. Process according to claim 1 or 2 wherein the hydrocarbon conversion process is alkylation.

8. Process according to claim 1 or 2 wherein the hydrocarbon conversion process is reforming.

9. Process according to claim 1 or 2 wherein the hydrocarbon conversion process is hydrotreating.

10. Process according to claim 1 or 2 wherein the hydrocarbon conversion process is isomerization.

11. Process according to claim 10 wherein the isomerization is xylene isomerization.

* * * * *